United States Patent
Bonde et al.

(10) Patent No.: US 8,550,743 B2
(45) Date of Patent: Oct. 8, 2013

(54) SLIDING LOCK DEVICE

(75) Inventors: Eric H. Bonde, Minnetonka, MN (US); Ahmed Elmouelhi, Plymouth, MN (US); Ross C. Gerber, Rice Lake, WI (US)

(73) Assignee: Medtronic, Inc., Minneapolis, MN (US)

( * ) Notice: Subject to any disclaimer, the term of this patent is extended or adjusted under 35 U.S.C. 154(b) by 1621 days.

(21) Appl. No.: 11/241,825

(22) Filed: Sep. 30, 2005

(65) Prior Publication Data

US 2007/0077827 A1    Apr. 5, 2007

(51) Int. Cl.
*F16B 21/02*    (2006.01)

(52) U.S. Cl.
USPC .......................................... 403/348; 403/349

(58) Field of Classification Search
USPC ................. 403/180, 238, 301, 317, 348, 349; 285/317, 298, 302; 606/101; 411/965, 411/970, 971
See application file for complete search history.

(56) References Cited

U.S. PATENT DOCUMENTS

| | | | |
|---|---|---|---|
| 1,489,310 A * | 4/1924 | Critchlow | |
| 1,997,858 A * | 4/1935 | Clawson | |
| 2,043,935 A * | 6/1936 | Stebbins | 285/305 |
| 2,317,729 A * | 4/1943 | Bruno | 403/348 |
| 3,124,373 A * | 3/1964 | Thomsen | |
| 3,538,940 A * | 11/1970 | Graham | 285/317 |
| 3,583,731 A * | 6/1971 | Jewell | |
| 3,663,808 A | 5/1972 | Baatz | |
| 3,929,356 A * | 12/1975 | DeVincent et al. | |
| 4,269,075 A * | 5/1981 | Crist et al. | 403/316 |
| 4,538,967 A * | 9/1985 | Furukawa | 403/349 |
| 4,541,457 A * | 9/1985 | Blenkush | 285/317 |
| 4,653,987 A | 3/1987 | Tsuji et al. | |
| 4,875,816 A * | 10/1989 | Peterson | 411/970 |
| 4,931,040 A * | 6/1990 | Haber et al. | |
| 5,005,878 A * | 4/1991 | Smith | 285/921 |
| 5,026,016 A * | 6/1991 | Lisowski | |
| 5,193,643 A * | 3/1993 | McIntyre | |
| 5,233,912 A * | 8/1993 | Mueller | 403/349 |

(Continued)

FOREIGN PATENT DOCUMENTS

| | | | |
|---|---|---|---|
| DE | 4209000 C1 | * | 5/1993 |
| SE | 199484 | * | 11/1965 |
| WO | WO 00/66015 | | 11/2000 |

OTHER PUBLICATIONS

Office Action dated Feb. 17, 2009 for U.S. Appl. No. 11/414,503 (11 pgs.).

(Continued)

*Primary Examiner* — Victor MacArthur (74) *Attorney, Agent, or Firm* — Shumaker & Sieffert, P.A.

(57) ABSTRACT

A system that is used to lock an accessory, for example a cystoscope that is locked to a hand held device that provides prostate ablation therapy, within a housing includes a sliding lock device (SLD) which receives and surrounds at least a portion of the cystoscope in an opening. Once the cystoscope is positioned within the SLD, the user may slide a cover to engage a tab of the cystoscope and secure the cystoscope within the SLD and the housing. The SLD also includes a mechanism for prohibiting cystoscope rotation. After the cystoscope is locked, the SLD allows for a defined amount of axial movement to facilitate prostate viewing and the deployment of prostate ablation therapy. Alternatively, the cover may slide in a rotational manner to secure the cystoscope.

33 Claims, 7 Drawing Sheets

(56) References Cited

U.S. PATENT DOCUMENTS

| | | | |
|---|---|---|---|
| 5,238,221 A * | 8/1993 | Schwaderer et al. | |
| 5,345,362 A | 9/1994 | Winkler | |
| 5,396,062 A | 3/1995 | Eisentraut et al. | |
| 5,405,228 A * | 4/1995 | Reid et al. | 411/183 |
| 5,421,489 A | 6/1995 | Holzner, Sr. et al. | |
| 5,458,596 A | 10/1995 | Lax et al. | |
| 5,537,343 A | 7/1996 | Kikinis et al. | |
| 5,540,681 A | 7/1996 | Strul et al. | |
| D373,193 S | 8/1996 | Luther | |
| 5,582,588 A | 12/1996 | Sakurai et al. | |
| 5,657,755 A | 8/1997 | Desai | |
| 5,660,529 A | 8/1997 | Hill | |
| D394,903 S | 6/1998 | Barkley et al. | |
| 5,765,877 A * | 6/1998 | Sakane et al. | 285/305 |
| 5,788,291 A * | 8/1998 | Williams et al. | 285/325 |
| 5,827,280 A | 10/1998 | Sandock et al. | |
| D402,758 S | 12/1998 | Barkley et al. | |
| 5,871,481 A | 2/1999 | Kannenberg et al. | |
| D411,622 S | 6/1999 | Hall | |
| 5,957,920 A | 9/1999 | Baker | |
| 5,964,756 A * | 10/1999 | McGaffigan et al. | |
| 5,975,820 A * | 11/1999 | Kirchen | |
| 5,997,528 A | 12/1999 | Bisch et al. | |
| D438,204 S | 2/2001 | Winkler | |
| 6,193,714 B1 * | 2/2001 | McGaffigan et al. | 606/45 |
| D441,450 S | 5/2001 | Salvatori et al. | |
| 6,231,089 B1 * | 5/2001 | DeCler et al. | 285/317 |
| 6,231,569 B1 | 5/2001 | Bek et al. | |
| 6,235,022 B1 | 5/2001 | Hallock et al. | |
| 6,238,391 B1 | 5/2001 | Olsen et al. | |
| 6,241,725 B1 | 6/2001 | Cosman | |
| 6,258,087 B1 | 7/2001 | Edwards et al. | |
| D447,241 S | 8/2001 | Deck | |
| 6,280,440 B1 | 8/2001 | Gocho | |
| 6,299,220 B1 * | 10/2001 | Dittrich et al. | 285/317 |
| 6,360,922 B1 * | 3/2002 | Englhard | 222/341 |
| 6,440,128 B1 | 8/2002 | Edwards et al. | |
| 6,458,121 B1 | 10/2002 | Rosenstock et al. | |
| D471,279 S | 3/2003 | Locke et al. | |
| 6,580,948 B2 | 6/2003 | Haupert et al. | |
| 6,642,274 B1 | 11/2003 | Neal | |
| 6,645,202 B1 | 11/2003 | Pless et al. | |
| 6,659,105 B2 | 12/2003 | Burbank et al. | |
| 6,659,106 B1 | 12/2003 | Hovda et al. | |
| 6,669,685 B1 | 12/2003 | Rizoiu et al. | |
| 6,671,558 B1 | 12/2003 | Soykan et al. | |
| D484,981 S | 1/2004 | Faller et al. | |
| 6,673,063 B2 | 1/2004 | Brett | |
| 6,676,658 B2 | 1/2004 | Burbank et al. | |
| 6,678,554 B1 | 1/2004 | Sun et al. | |
| 6,685,702 B2 | 2/2004 | Quijano et al. | |
| 6,689,128 B2 | 2/2004 | Sliwa, Jr. et al. | |
| 6,690,976 B2 | 2/2004 | Fenn et al. | |
| 6,706,039 B2 | 3/2004 | Mulier et al. | |
| 6,719,755 B2 | 4/2004 | Sliwa, Jr. et al. | |
| 6,752,767 B2 | 6/2004 | Turovskiy et al. | |
| 6,764,487 B2 | 7/2004 | Mulier et al. | |
| 6,805,128 B1 | 10/2004 | Pless et al. | |
| 6,805,129 B1 | 10/2004 | Pless et al. | |
| D499,183 S | 11/2004 | Vaisnys et al. | |
| 6,849,073 B2 | 2/2005 | Hoey et al. | |
| 6,852,091 B2 | 2/2005 | Edwards et al. | |
| 6,855,141 B2 | 2/2005 | Lovewell | |
| 6,932,811 B2 | 8/2005 | Hooven et al. | |
| D509,900 S | 9/2005 | Barnes et al. | |
| D538,432 S | 3/2007 | Diener et al. | |
| 7,325,839 B2 * | 2/2008 | Slentz | |
| 2002/0019612 A1 | 2/2002 | Watanabe et al. | |
| 2002/0040221 A1 | 4/2002 | Paddock et al. | |
| 2002/0058933 A1 | 5/2002 | Christopherson et al. | |
| 2002/0183740 A1 | 12/2002 | Edwards et al. | |
| 2002/0198504 A1 | 12/2002 | Risk, Jr. et al. | |
| 2003/0093503 A1 | 5/2003 | Yamaki et al. | |
| 2003/0138334 A1 | 7/2003 | Vandlik et al. | |
| 2003/0144653 A1 | 7/2003 | Francischelli et al. | |
| 2003/0171672 A1 | 9/2003 | Varghese et al. | |
| 2003/0216724 A1 | 11/2003 | Jahns | |
| 2004/0006337 A1 | 1/2004 | Nasab et al. | |
| 2004/0082946 A1 | 4/2004 | Malis et al. | |
| 2004/0176984 A1 | 9/2004 | White et al. | |
| 2004/0232022 A1 | 11/2004 | Killinger et al. | |
| 2004/0267340 A1 | 12/2004 | Cioanta et al. | |
| 2005/0010206 A1 | 1/2005 | Nasab et al. | |
| 2005/0080464 A1 | 4/2005 | Osborn et al. | |
| 2005/0192651 A1 | 9/2005 | Walneck et al. | |
| 2005/0245923 A1 | 11/2005 | Christopherson et al. | |
| 2006/0089636 A1 | 4/2006 | Christopherson et al. | |
| 2006/0241518 A1 | 10/2006 | Boese et al. | |
| 2006/0253176 A1 | 11/2006 | Caruso et al. | |
| 2006/0293727 A1 | 12/2006 | Spooner et al. | |
| 2007/0027510 A1 | 2/2007 | Rodrigues et al. | |
| 2007/0083193 A1 | 4/2007 | Werneth et al. | |
| 2007/0138213 A1 * | 6/2007 | Shanklin et al. | 222/385 |
| 2007/0276606 A1 | 11/2007 | Radkov et al. | |
| 2008/0039833 A1 * | 2/2008 | Catanese et al. | 606/46 |
| 2008/0039876 A1 * | 2/2008 | Catanese et al. | 606/151 |

OTHER PUBLICATIONS

Responsive Amendment dated Jun. 17, 2009 for U.S. Appl. No. 11/414,503 (13 pgs.).
Office Action dated Jun. 10, 2009 for U.S. Appl. No. 11/414,623 (19 pgs.).
Office Action dated Jun. 11, 2009 for U.S. Appl. No. 11/414,613 (20 pgs.).
Responsive Amendment dated Sep. 11, 2009 for U.S. Appl. No. 11/414,613 (21 pgs.).
Office Action dated Oct. 9, 2009 for U.S. Appl. No. 11/414,503 (11 pgs.).
Responsive Amendment dated Jan. 8, 2010 for U.S. Appl. No. 11/414,503 (13 pgs.).
Office Action dated Nov. 30, 2009 for U.S. Appl. No. 11/414,613 (24 pgs.).
Responsive Amendment dated Mar. 1, 2010 for U.S. Appl. No. 11/414,613 (15 pgs.).
Final Office Action dated Apr. 28, 2010 for U.S. Appl. No. 11/414,613, 27 pages.
Final Office Action for U.S. Appl. No. 11/414,503, mailed May 3, 2010, 11 pages.
Office Action from U.S. Appl. No. 12/938,829, dated Apr. 11, 2011, 15 pages.
Response to Office Action dated Apr. 11, 2011, from U.S. Appl. No. 12/938,829, filed Jul. 7, 2011, 8 pages.
Final office action for U.S. Appl. No. 12/938,829, mailed Sep. 27, 2011, 14 pages.
Response to final office action for U.S. Appl. No. 12/938,829, filed Nov. 22, 2011, 7 pages.

* cited by examiner

SLIDING LOCK DEVICE

TECHNICAL FIELD

The invention relates to connectors and, more particularly, to devices for securely attaching accessories.

BACKGROUND

Medical devices commonly include a wide variety of accessories to support patient needs and physician preferences. These accessories must be removable or replaceable to ensure sterile conditions between patients and procedures. In addition, disposable devices may interface with non-disposable equipment. Connectors are integral to the function of medical devices and the use of appropriate attachments.

For example, cystoscopes are commonly used to examine the urethra and bladder for treating benign prostate hyperplasia (BPH) in men. BPH is a condition caused by the second period of continued prostate gland growth. This growth begins after a man is approximately 25 years old and may begin to cause health problems after 40 years of age. The prostate growth eventually begins to constrict the urethra and may cause problems with urination and bladder functionality. Minimally invasive techniques include inserting a needle through the urethra to place the needle at the prostate site. Once positioned correctly, the needle is heated to ablate the prostate tissue to reduce the tissue volume and treat BPH.

A physician performs this procedure with a hand held device for inserting the needle and providing the therapeutic energy. The physician also uses a cystoscope to view inside of the urethra to correctly place the needle for proper therapy. In this example, a connector is used which allows the cystoscope to interface with the hand held device and reduce procedure time and increase treatment efficacy.

SUMMARY

The disclosure describes a system that is used to lock an accessory within a device. For example, the accessory is a cystoscope that is locked to a hand held device that provides prostate ablation therapy. The system includes a sliding lock which receives and surrounds at least a portion of the cystoscope in an opening. Once the cystoscope is positioned within the sliding lock device (SLD), the user may slide a cover in one direction to engage a tab of the cystoscope and secure the cystoscope within the SLD. The SLD also includes a mechanism for prohibiting cystoscope rotation. After the cystoscope is locked, the SLD allows for a defined amount of axial movement to facilitate prostate viewing and the deployment of prostate ablation therapy. Alternatively, the cover may slide in a rotational manner to secure the cystoscope.

Physicians prefer devices that are easy to use while providing safe and effective treatment for their patients. A simple device that is capable of locking an accessory such as a cystoscope may decrease treatment time and allow the physician to focus on the treatment.

In one embodiment, the disclosure is directed to a system for releasably attaching a device to a housing comprising an elongate collar comprising a longitudinal bore, wherein a first end of the collar engages an opening in the housing, and wherein the collar is slideable within the opening in the housing and along a longitudinal axis of the bore of the collar, a collar flange on a second end of the collar comprising a substantially planar first mating surface, wherein the collar flange and first mating surface is substantially normal to the longitudinal axis of the bore of the collar, and a cover comprising a substantially planar second mating surface and a pair of sidewalls substantially parallel to the second mating surface in which the sidewalls form channels for engaging the collar flange, and wherein the second mating surface slides in a place over the first mating surface.

In another embodiment, the disclosure is directed to system for releasably attaching a device comprising an elongate collar comprising a longitudinal bore, wherein a first end of the collar comprises at least one retaining structure that extends in a direction normal to a longitudinal axis of the bore of the collar, a collar flange on a second end of the collar comprising a substantially planar first mating surface, wherein the collar flange and first mating surface is substantially normal to the longitudinal axis of the bore of the collar, and a cover comprising a substantially planar second mating surface and a pair of sidewalls substantially parallel to the second mating surface in which the sidewalls form channels for engaging the collar flange, wherein the second mating surface comprises an opening, and wherein the second mating surface slides in a plane over the first mating surface.

In an alternative embodiment, the disclosure is directed to a system for releasably attaching a device comprising an elongate collar comprising a longitudinal bore, wherein a first end of the collar comprises at least one retaining structure that extends in a direction normal to a longitudinal axis of the bore of the collar, a collar flange on a second end of the collar comprising a substantially planar first mating surface, wherein the collar flange and first mating surface is substantially normal to the longitudinal axis of the bore of the collar, and wherein a first portion of the collar flange is attached to the second end of the collar, and a cover comprising a substantially planar second mating surface coupled to the first portion of the collar flange, wherein the second mating surface comprises an opening.

In various embodiments, the SLD may provide one or more advantages. For example, the SLD can be operated with only one hand as force is applied in just one direction to lock or unlock the device. The SLD prohibits cystoscope rotation while allowing for a defined amount of axial movement useful when providing therapy. The SLD also may accept any Storz compatible cystoscope that a physician prefers to use. In addition, the SLD is easily manufactured and assembled from a wide variety of injection moldable plastics and is inexpensive to produce.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
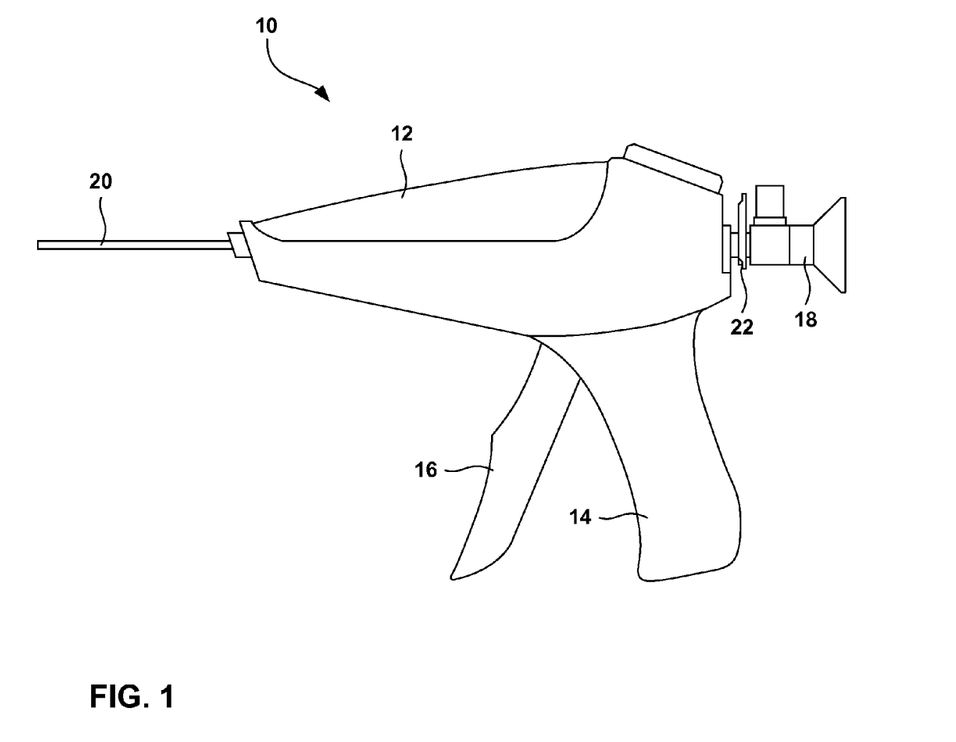
FIG. 1 is a conceptual diagram illustrating an exemplary cystoscope locked into a hand held device.

FIG. 1 is a conceptual diagram illustrating exemplary cystoscope 18 locked into a hand held device. As shown in FIG. 1, system 10 includes housing 12 which is attached to handle 14 and trigger 16. Cystoscope 18 includes probe 20 and is locked within housing 12 by sliding lock device (SLD) 22. In this exemplary embodiment, system 10 is utilized for the treatment of benign prostatic hyperplasia (BPH). A physician holds handle 14 and trigger 16 to guide probe 20 through a urethra. The physician uses the cystoscope to view the urethra through probe 20 and locate a prostate for positioning a needle (not shown) into the prostate from a catheter (not shown) adjacent to probe 20. Once the physician identifies correct placement for the needle, trigger 16 is squeezed toward handle 14 to extend the needle into the prostate.

With the exception of cystoscope 18, system 10 is coupled to a radio frequency (RF) generator (not shown) that provides the energy used to ablate the prostate tissue. System 10 may also be coupled to a fluid delivery device (not shown) which may irrigate the treatment site with the fluid. Cystoscope 18 is an accessory and is not permanently disposed within housing 12. The cystoscope 18 is typically an expensive, non-disposable instrument with many different designs. Physician preferences vary widely, so a removable cystoscope may be necessary for treatment efficacy.

Probe 20 of cystoscope 18 may be inserted into an opening running the length of housing 12. SLD 22 also resides within the opening to surround a portion of cystoscope 18. Once cystoscope 18 is inserted into housing 12, the physician may push SLD 22 into the locked conformation of the SLD which prevents cystoscope 18 from moving with respect to SLD 22. SLD 22 does permit a defined amount of axial movement along the longitudinal axis of the opening in housing 12 between SLD 22 and the housing. This axial movement allows the physician to view the urethra when cystoscope 18 is pushed close to housing 12 and view needle placement in front of probe 20 when cystoscope is moved away from housing 12.

SLD 22 may provide certain advantages to the physician in operating system 10. The physician may lock SLD 22 with only one hand, instead of using two hands to secure cystoscope 18 within housing 12. SLD 22 also uses male locking structures, detents, and female locking structures, indents, to lock the SLD in either open or closed positions. While cystoscope 18 is secured within housing 12, a defined amount of axial movement allows a small degree of flexibility to facilitate the treatment.

Housing 12, handle 14 and trigger 16 are constructed of a lightweight molded plastic such as polystyrene. In other embodiments, other injection molded plastics may be used such as polyurethane, polypropylene, high molecular weight polyurethane, polycarbonate or nylon. Alternatively, construction materials may be aluminum, stainless steel, a metal alloy or composite material. In addition, housing 12, handle 14 and trigger 16 may be constructed of different materials instead of being constructed out of the same material. In some embodiments, housing 12, handle 14 and trigger 16 may be assembled through snap fit connections, adhesives or mechanical fixation devices such as pins or screws.

Cystoscope 18 may be any type of cystoscope or similar internal viewing device. The length of probe 20 may vary with respect to the intended procedure. In some embodiments, any scope with a Storz (Karl Storz, Germany) compatible locking design may be used. In other embodiments, SLD 22 may be located at the opposite end of housing 12 to be compatible with a certain type of cystoscope or facilitate ease of operation for the physician.

While the exemplary system 10 illustrates SLD 22 within housing 12 to secure cystoscope 18, SLD 22 may be used in any type of system to secure an accessory. For example, SLD 22 may be used to secure any type of scope or catheter to be inserted within a patient. In other embodiments, SLD 22 may be used to lock electrical cables, fluid lines, or any other system where simple and quick locking is beneficial to the system function. System 10 as described in FIG. 1 will be used as an example of SLD 22 herein.

Figure 2A:
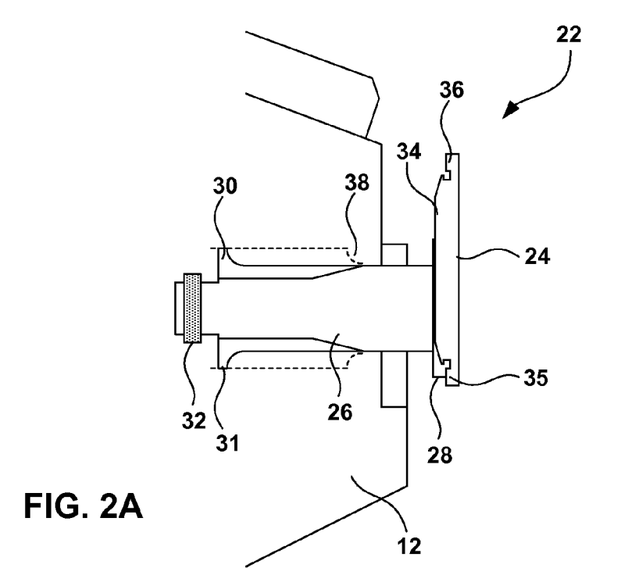
FIGS. 2A and 2B are side views of an exemplary sliding lock in two different positions with respect to a hand held device.
Figure 2B:
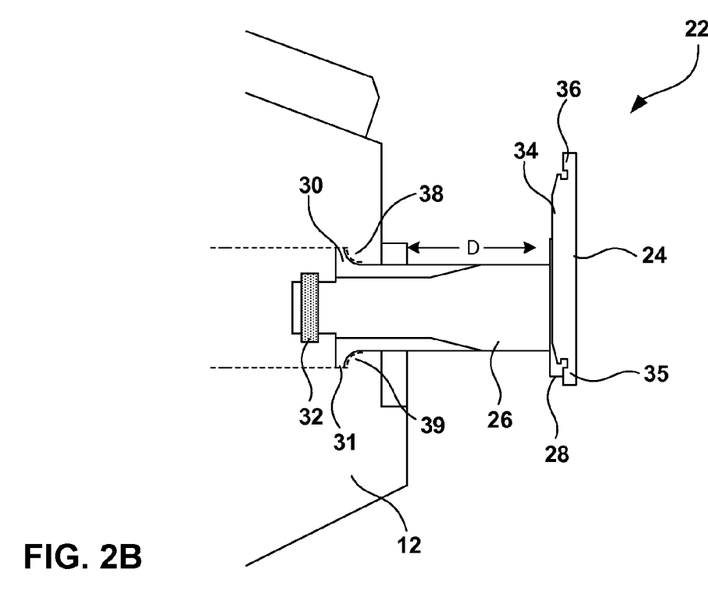

FIGS. 2A and 2B are side views of exemplary SLD 22 in two different positions with respect to housing 12. As shown in FIG. 2A, SLD 22 is located within housing 12 in the retracted position. The retracted position is used by the physician to navigate through the urethra. SLD 22 includes cover 24 coupled to collar flange 28. Cover 24 includes limit flanges 35 and 36 and sidewall 34. Collar flange 28 is attached to collar 26 which contacts the opening of housing 12. Collar 26 includes retaining tabs 30 and 31 and o-ring 32. Retaining tab 30 contacts bumper 38 to prohibit collar 26 from sliding out of housing 12.

Cover 24 is in the locked conformation to hold cystoscope 18 securely. Limit flange 35 prevents cover 24 from sliding off of collar flange 28. Limit flange 36 also prevents cover 24 from sliding off of collar flange 28 at the opposing end of the cover. Limit flanges 35 and 36 are curved to match the ends of cover 24 and collar flange 28. In some embodiments, limit flanges 35 and 36 may be any shape or size necessary to prevent cover 24 from becoming unattached from collar flange 28.

Sidewall 34 is opposite of and parallel to another sidewall (not shown) which couples cover 24 to collar flange 28. Sidewall 34 allows cover 24 to move with respect to collar flange 28 in one dimension. This movement allows cover 24 to open or lock cystoscope 18 within SLD 22. In some embodiments, collar flange 28 includes a guide structure for engaging sidewall 34. The guide structure may comprise one or more guide tabs which contact sidewall 34, where the guide tabs are thinner than the thickness of collar flange 28.

As the physician uses system 10, cystoscope 18 may be handled separately from housing 12 or handle 14. SLD 22 may prevent rotation of cystoscope 18 with respect to housing 12. In some embodiments, retaining tabs 30 and 31 prevent collar 26 from rotating within housing 12. Retaining tabs 30 and 31 may glide along rails within housing 12 to provide torque resistance along the entire sliding length of collar 26. In other embodiments, more or less retaining tabs may be used to control torque that induces rotation of SLD 22.

O-ring 32 is attached to collar 26 and resides within housing 12. O-ring 32 contacts a least a portion of the opening within housing 12 to provide some resistance to moving collar 26 within the opening of housing 12. O-ring 32 may be constructed out of a soft plastic or rubber compound. In some embodiments, the material or thickness of o-ring 32 may vary to change the force required to move collar 26 within the opening of housing 12.

FIG. 2B shows SLD 22 in the similar locked conformation as shown in FIG. 2A. However, FIG. 2B displays the movement capable of SLD 22 within the opening of housing 12 as SLD 22 is shown in the extended position. After the physician has located the intended prostate site, cystoscope 18 may be pulled back a distance D to enable the physician to watch the needle enter the prostate tissue.

Since cystoscope 18 is locked within SLD 22, a pulling force on cystoscope 18 overcomes the static friction of o-ring 32 and causes collar 26 to slide within the opening. Retaining tabs 30 and 31 contact bumpers 38 and 39, respectively, to prohibit SLD 22 from being removed from housing 12. In some embodiments, bumpers 38 and 39 may be positioned at different locations within housing 12. For example, housing 12 may position bumpers 38 and 39 further from the edge of housing 12 to allow SLD 22 to move a shorter distance D.

Alternatively, bumpers 38 and 39 may be located closer to the edge of housing 12 to allow movement greater than distance D.

SLD 22 allows cystoscope 18 to be removed from the SLD at any location of the SLD with respect to housing 12. Collar 26 may be in the retracted, extended, or any other position when cystoscope 18 is added to or removed from SLD 22. In some embodiments, cover 24 may not move up and down to lock or unlock cystoscope 18. Cover 24 may slide in any direction within a plane, such as horizontally or diagonally, to lock and unlock cystoscope 18.

SLD 22 may be constructed of an injection moldable material with some degree of flexibility. The preferred material of SLD 22 is acrylonitrile butadiene styrene (ABS) due to its flexibility, strength and shape holding properties. Other possible materials which may be used to construct at least part of SLD 22 may include polyurethane, polypropylene, polycarbonate, nylon or other polystyrene polymers. Composites or flexible metal alloys including titanium or nitinol may be used to construct SLD 22 in some embodiments.

Figure 3A:
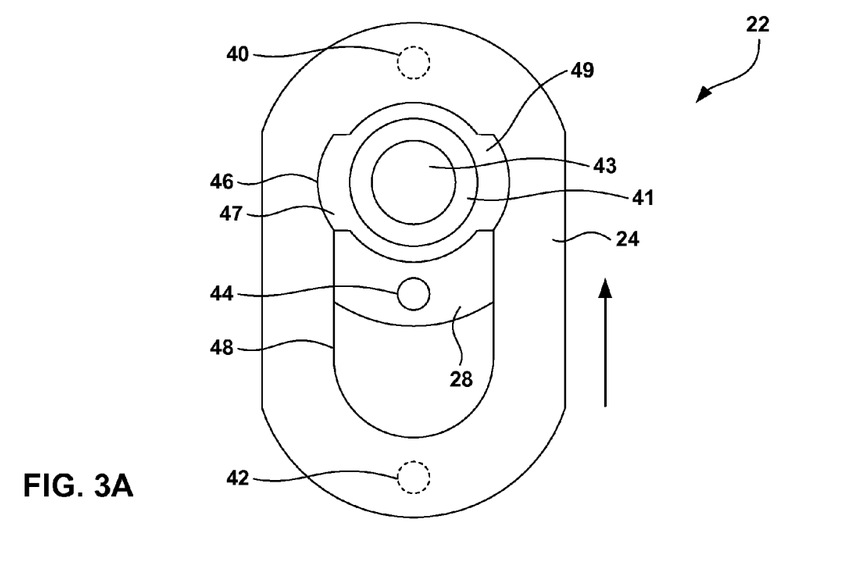
FIGS. 3A and 3B are front views of an exemplary sliding lock in open and locked configurations.
Figure 3B:
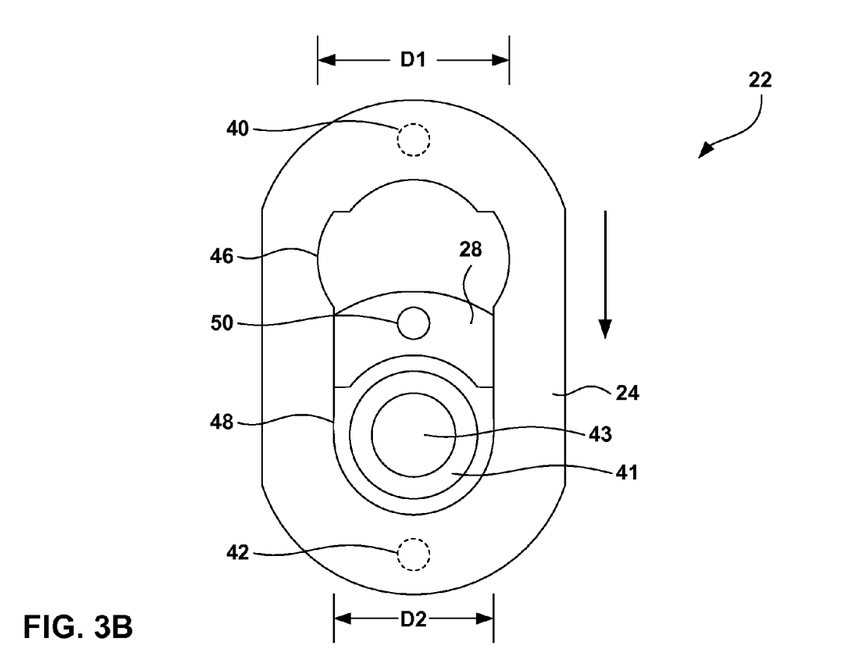

FIGS. 3A and 3B are front views of SLD 22 in unlocked and locked configurations. As shown in FIG. 3A, SLD 22 includes cover 24 in the unlocked conformation covering collar flange 28. Receiving channel 41 funnels down to bore 43 to facilitate insertion of cystoscope 18 into housing 12 through SLD 22. Collar flange 28 includes detent 44, detent 50 (shown in FIG. 3B), slot 47 and slot 49, where a detent is a male locking structure. Cover 24 includes indents 40 and 42, where an indent is a female locking structure. Cover also defines unlock edge 46 and lock edge 48. The arrow in FIG. 3A indicates the direction cover 24 moves to lock cystoscope 18 in place within SLD 22, while the arrow in FIG. 3B indicates the direction cover 24 moves to unlock cystoscope 18 from SLD 22.

Collar flange 28 is attached to collar 26 which forms receiving channel 41 and bore 43. Collar flange 28 forms slots 47 and 49 which accept corresponding tabs from cystoscope 18. Slots 47 and 49 include an outside curved edge and parallel sides to prevent cystoscope 18 from rotating within SLD 22. In some embodiments, more or less slots may be formed by collar flange 28 which correspond to tabs of the accessory to be inserted into SLD 22. In other embodiments, slots 47 and 49 may be formed into another shape such as a rectangle, triangle, or other shape to accept tabs from an accessory.

Collar flange 28 also includes substantially similar detents 44 and 50 (shown in FIG. 3B). Detent 44 is round in shape and extends spherically outward from the first mating surface towards cover 24 which includes the second mating surface. Detent 44 provides the locking force to lock sliding cover 24 in place within respect to collar flange 28. Indent 40 is mated with detent 50 in the unlocked conformation shown. As cover 24 slides in the direction of the arrow, the cover flexes slightly to move over detent 44 until indent 42 mates over detent 44. Once detent 44 and indent 42 mate, cover 24 is locked in place until the physician provides enough force to the cover in the direction of sliding to overcome the bending modulus of the cover and separate the detent from the indent.

In some embodiments, detents 44 and 50 and indents 40 and 44 may be formed into a non-spherical shape. Some shapes of detents and indents may include cubes, trapezoids, cylinders, pyramids, or any other three-dimensional shape. In other embodiments, the sizes of mating detents and indents may not be the same while still performing the function of the detent and indent relationship. Additionally, the size of detents 44 and 50 and indents 40 and 42 may differ. SLD 22 may include more or less than two sets of indents and detents.

The force required to lock or unlock SLD 22 is generally between 0.1 lbf and 16.5 lbf. Preferably, the force required to lock or unlock SLD 22 is between 0.3 lbf and 1.0 lbf. Ideally, the force required to lock or unlock SLD 22 is between 0.5 lbf and 0.8 lbf. These forces may be applied to overcome the mating of an indent and detent or overcome any other locking mechanism of SLD 22 as described herein.

Cover 24 is the component responsible for unlocking and locking cystoscope 18 from SLD 22. Cover 24 defines unlock edge 46 and lock edge 48 which partially form the main opening of the cover. Unlock edge 46 permits the tabs of cystoscope 18 to pass through cover 24 and into slots 47 and 49. Curved unlock edge 46 has a diameter of D1. In some embodiments, unlock edge 46 may be larger than necessary to accept the tabs of cystoscope 18. Since unlock edge 46 does not need to contact any area of cystoscope 18, the shape and size of unlock edge 46 may not conform to the size and shape of tabs on cystoscope 18.

Lock edge 48 of cover 24 has a diameter of D2, where D2 is less than D1. Lock edge 48 slides over the tabs of cystoscope 18 to lock the cystoscope within SLD 22. The inner side of lock edge 48 may or may not contact the side of cystoscope 18 to generate a secure lock. As described above, detent 44 mates with indent 42 to hold lock edge 48 of cover 24 in place. In other embodiments, detents and indents may not be used to lock cover 24 in place. Lock edge 48 may contact a side of an accessory with enough force to provide a secure friction fit. In other embodiments, lock edge 48 could be slightly curved or include a different locking structure that contacts the accessory to lock cover 24 in place and secure the accessory within SLD 22.

FIG. 3B shows cover 24 in the locked confirmation, wherein an accessory would be secured within SLD 22. Indent 42 is mated with detent 44 (shown in FIG. 3A) and detent 50 on the first mating surface of collar flange 28 is visable. In the examples of FIG. 3A and FIG. 3B, cover 24 moves up to lock an accessory and down to unlock the accessory. Alternatively, cover 24 may be inverted and mated to collar 28 so that cover 24 is moved down to lock the accessory within SLD 22.

In some embodiments, cover 24 may be a different length so that the cover moves less or more in order to change the conformation of SLD 22 from unlocked to locked. Cover 24 size may be related to the specific accessory to be locked in SLD 22. Alternatively, SLD 22 may be shaped to allow cover 24 to slide from left to right or right to left to change the locked conformation of the SLD.

In other embodiments, detent 50 may instead be a small hole in collar flange 28 that accepts a post of an accessory. In the case of an accessory which includes a post for alignment or connectivity with a connector such as SLD 22, the small hole in collar flange 28 may receive the post to allow SLD 22 to be compatible with such an accessory. The post and small hole relationship may or may not function to assist securing the accessory within SLD 22.

Figure 4:
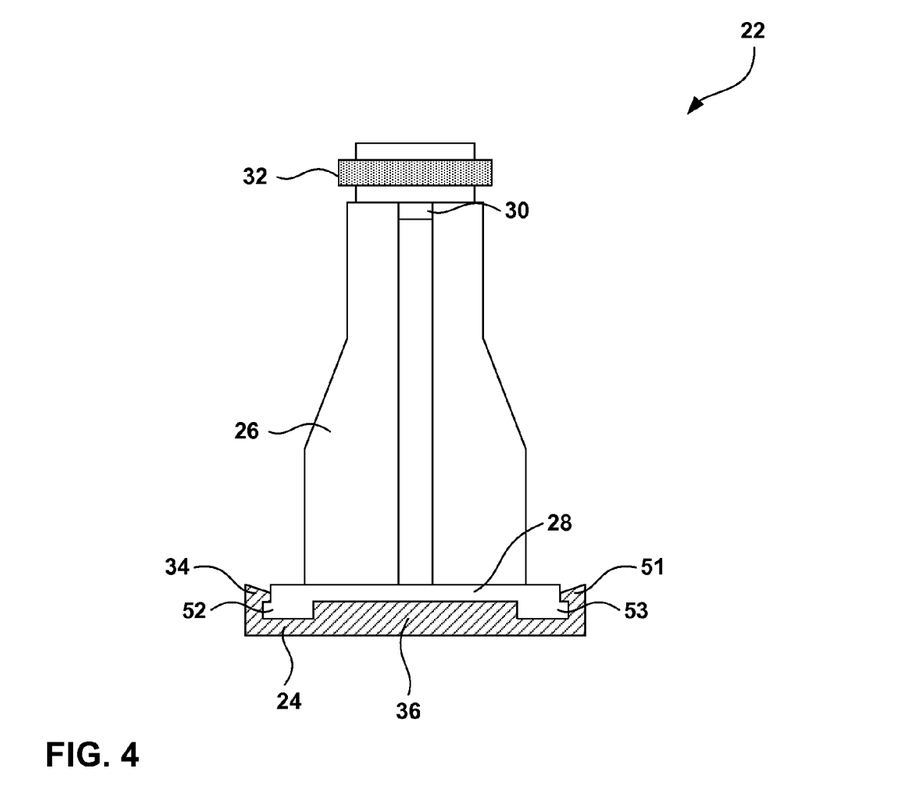
FIG. 4 is a top view of an exemplary sliding lock removed from a hand held device.

FIG. 4 is a top view of SLD 22 removed from housing 12. As shown in FIG. 4, collar 26 includes retaining tab 30 and o-ring 32. Collar 26 is attached to collar flange 28 in which the first mating surface is in contact with the second mating surface of cover 24. Collar flange 28 comprises guide tabs 52 and 53 which are engaged by sidewalls 34 and 51. Sidewalls 34 and 51 also include retaining flanges 55 and 57 which extend normal to each sidewall to encompass each respective guide tab. Limit flange 36 is also shown attached to cover 24.

Sidewalls 34 and 51 use a retaining flange to clamp on the guide tabs 52 and 53. In this manner, bending of cover 24 as detents and indents mated or separated does not cause separation of cover 24 from collar flange 28. In some embodiments, collar flange 28 may not comprise guide tabs 52 and 53 for sidewalls 34 and 51 to engage. Sidewalls 34 and 51 may extend to a greater length and engage the edges of collar flange 28. In other embodiments, sidewalls 34 and 51 may not comprise retaining flanges 55 and 57. Sidewalls 34 and 51 may form acute angles with cover 24 to engage acute parallel surfaces of the edge of collar flange 28. Angled sidewalls 34 and 51, or other shapes, may perform the functional relationship between cover 24 and collar flange 28.

Figure 5:
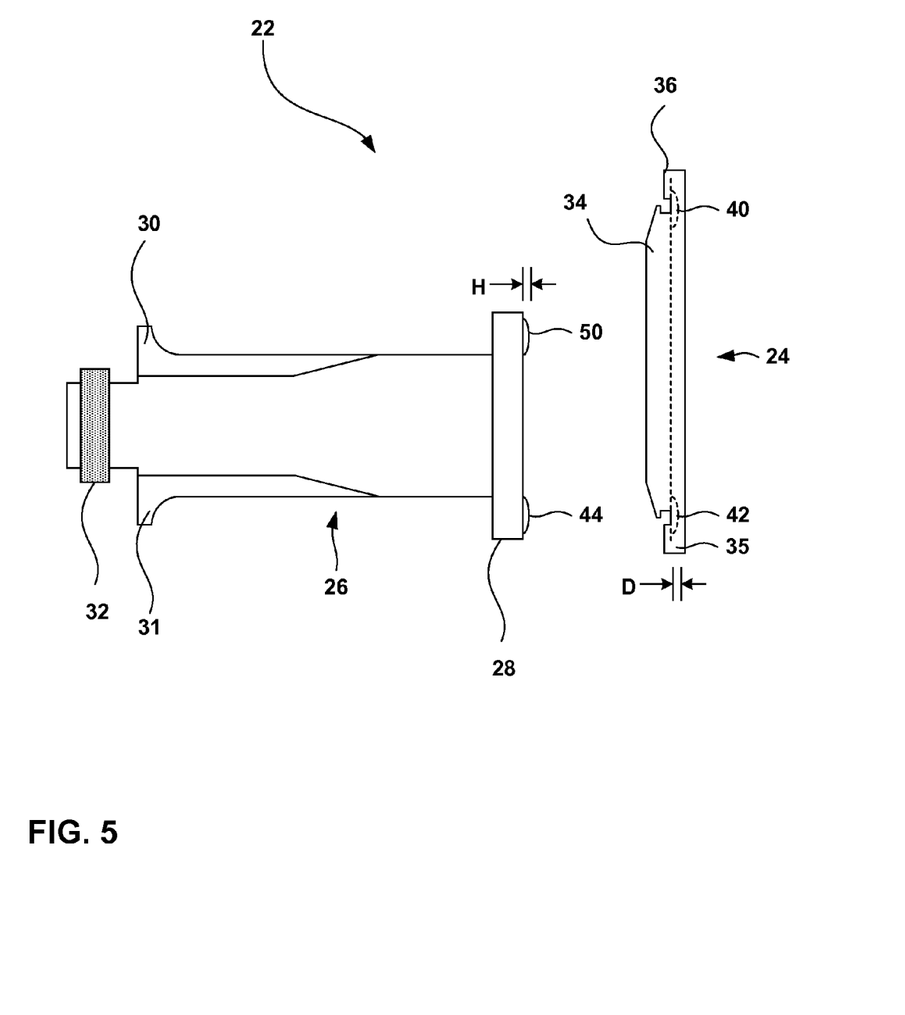
FIG. 5 is side view of two components of an exemplary sliding lock.

FIG. 5 is side view of the components of SLD 22. As shown in FIG. 5, collar 26 and collar flange 28 are separated from cover 24. Separating the first mating surface of collar flange 28 from the second mating surface of cover 24 illustrates the male and female locking structures for locking cover 24 in place with respect to collar flange 28.

Detents 44 and 50 are attached to collar flange 28 while indents 40 and 42 are formed into cover 24. Detents 44 and 50 are raised a height H above the first mating surface of collar flange 28. Indents 40 and 42 are set a depth D into the second mating surface of cover 24. In the preferred embodiment, height H and depth D are equal to provide optimal mating between each detent and indent pair. However, height H and depth D may be different from one another depending on the application of SLD 22. Alternatively, dimensions may vary between detents 44 and 50 or indents 40 and 42.

In general, height H and depth D may be between 0.005 inches and 0.050 inches. Preferably, height H and depth D may be between 0.010 inches and 0.035 inches. Ideally, height H and depth D may be approximately 0.020 inches. Modifying height H and depth D changes the force required to lock or unlock cover 24 from collar flange 28. For example, a greater height H and depth D may require a greater force to lock or unlock cover 24 while a smaller height H and depth D may require less force to operate the lock. Preferred forces to operate SLD 22 are further described in FIG. 3A.

Figure 6A:
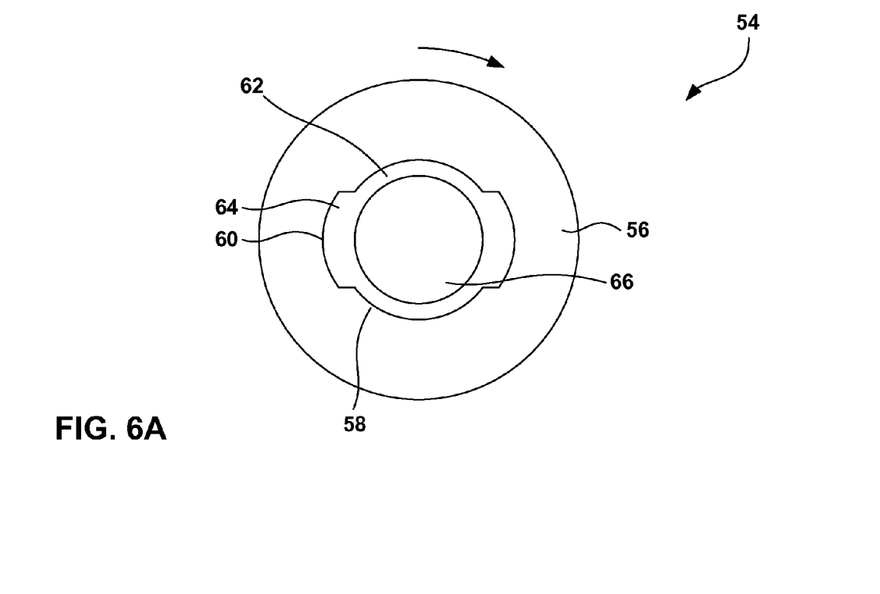
FIG. 6A and 6B are front views of an alternative sliding lock device.
Figure 6B:
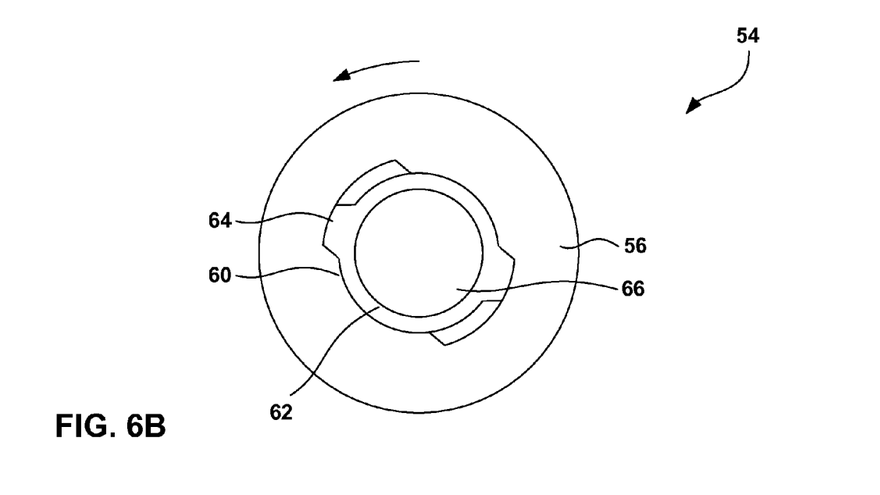

FIGS. 6A and 6B are front views of alternative rotating lock device (RLD) 54. As shown in FIG. 6A, RLD 54 includes collar 62 which is substantially similar to collar 26 and collar flange 28 of SLD 22. Collar 62 includes a substantially circular flange, slot 64 and longitudinal bore 66; however, a partially circular flange similar to collar flange 28 may be used as well. Cover 56 includes unlock edge 60 and lock edge 58. Cover 56 also includes a plurality of sidewalls (not shown) extending normal to cover 56 surface for engaging the circular flange of collar 62 (not shown). RLD 54 is shown in the unlocked conformation in FIG. 6A.

Cover 56 is mated to the collar flange similar to SLD 22, except that cover 56 slides circumferentially, or rotates, with respect to the collar flange to lock an accessory within RLD 54. An accessory, such as cystoscope 18, is inserted into bore 66 and tabs or the cystoscope fit into slot 64 within unlock edge 60. The physician rotates cover 56 in the direction of the arrow to slide lock edge 58 of the cover to lock the tabs of cystoscope 18 within RLD 54. In the preferred embodiment, cover 56 may rotate in either direction indefinitely. In other embodiments, one or more limit flanges of cover 56 only allow cover 56 to move in one direction to lock and in another direction to unlock.

FIG. 6B illustrates RLD 54 in the locked configuration. Lock edge 58 of cover 56 traps the tabs of cystoscope 18 to secure the cystoscope in place. Cover 56 may continue to rotate clockwise to fully trap the tab of cystoscope 18 in slot 64. Cover 56 may be rotated in the direction of the arrow in FIG. 6B to unlock cystoscope 18 from RLD 54.

In some embodiments, RLD 54 may utilize male and female locking structures such as the detents and indents of SLD 22. These locking structures may be located at positions between cover 56 and the collar flange of collar 62. The positions may be in the plane of cover 56 rotation or along the circumferential edge normal to the plane of rotation along cover 65. Locking RLD 54 into certain confirmations may be beneficial to unwanted unlocking of cystoscope 18 during a procedure.

Figure 7A:
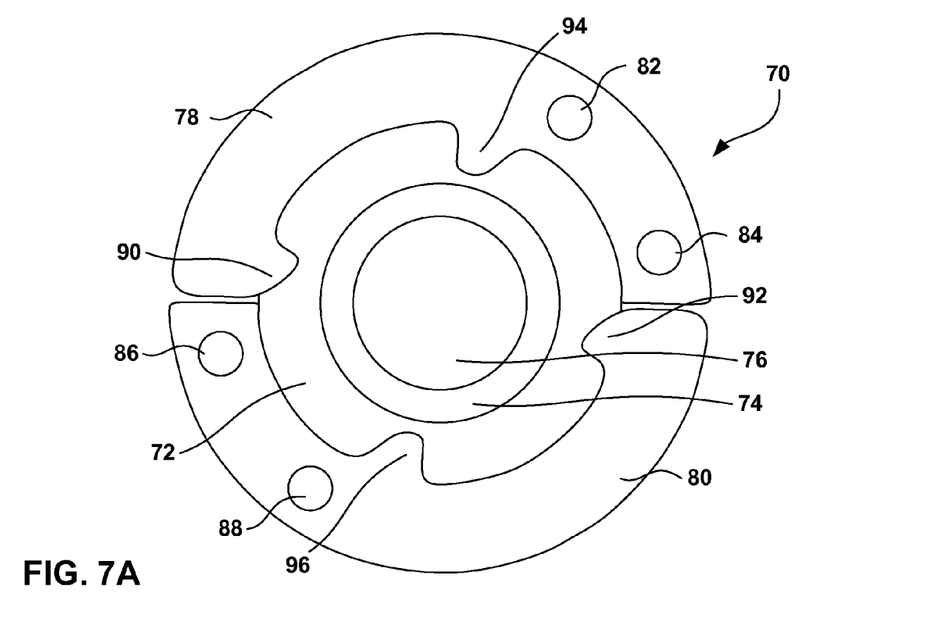
FIG. 7A and 7B are front views of a snapping lock device.
Figure 7B:
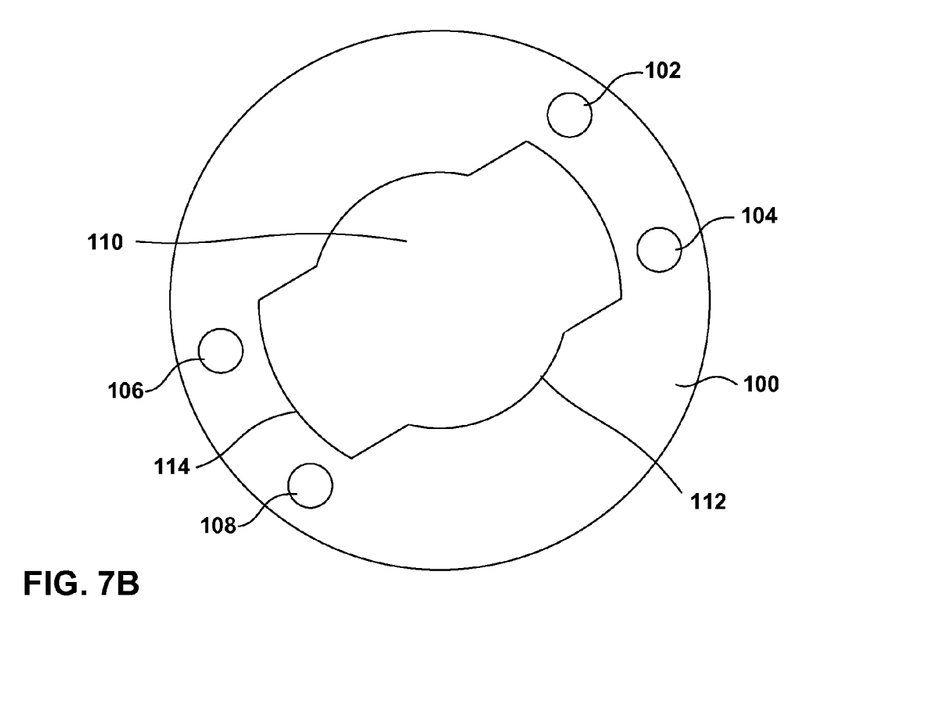

FIGS. 7A and 7B are front views of alternative snapping lock device (SLD) 70.

As shown in FIG. 7A, SLD 72 includes collar 72, receiving channel 74 and bore 76 which are substantially similar to collar 26, receiving channel 41 and bore 43 of SLD 22. Collar flanges 78 and 80 are attached to collar 72. Collar flange 78 includes ramped tab 90, limit tab 94, and mounting holes 82 and 84. Similarly, collar flange 80 includes ramped tab 92, limit tab 96, and mounting holes 86 and 88.

Collar flanges 78 and 80 are only attached to collar 72 by the first portion of each collar flange comprising respective mounting holes 82, 84, 86 and 88 and limit tabs 94 and 96. The second portion of each collar flange comprises ramped tabs 90 and 92. The second portion of each collar flange is attached to any other structure, so each collar flange is capable of flexing radially outward when force is applied to each collar flange.

For example, cystoscope 18 includes two opposite tabs which each fit between the ramped tab of one collar flange and the limit tab of the other collar flange. As cystoscope 18 is rotated clockwise, force is applied to ramped tabs 90 and 92 which cause collar flanges 78 and 80 to flex radially outward until the each ramped tab 90 and 92 snaps back into place indicating that each tab fits between the ramped tab and limit tab of one collar flange. In this locked position, cystoscope 18 cannot rotate within SLD 70. A cover (FIG. 7B) is also used to lock cystoscope 18.

Thickness of collar flanges 78 and 80 and the shape of ramped tabs 90 and 92 change the force required to rotate and lock cystoscope 18, or another accessory, into place. Counterclockwise rotation of cystoscope 18 forces collar flanges 78 and 80 to flex outward again in order to remove the cystoscope from SLD 70.

FIG. 7B illustrates cover 100 which is part of SLD 70. Cover 100 includes opening 110 which is partially outlined by lock edge 112 and unlock edge 114. Mounting holes 102, 104, 106 and 108 align with mounting holes 82, 84, 86 and 88 of collar flanges 78 and 80. Pins, screws or other fastening devices are used to attach cover 100 to collar flanges 78 and 80. Cover 100 is mounted to collar flanges 78 and 80 before cystoscope 18 is locked into place. Similar to collar flange 28 and cover 24, collar flanges 78 and 80 create the first mating surface in contact with the second mating surface of cover 100 when cover 100 is attached to collar flanges 78 and 80.

In the provided embodiment, cystoscope 18 rotated clockwise to lock and counterclockwise to unlock. In other embodiments, cystoscope may be rotated counterclockwise to lock and clockwise to unlock. In either case, cover 100 prevents cystoscope 18 from being removed from SLD 70.

The preceding specific embodiments are illustrative of the practice of the invention. It is to be understood, therefore, that other expedients known to those skilled in the art or disclosed herein may be employed without departing from the invention or the scope of the claims.

Many embodiments of the invention have been described. Various modifications may be made without departing from the scope of the claims. These and other embodiments are within the scope of the following claims.

The invention claimed is:

1. A system for releasably attaching a removable device, the system comprising:
an elongate collar comprising a longitudinal bore having a longitudinal axis, wherein:
a first end of the collar is configured to engage an opening in a housing of a medical device;
the collar is configured to be slideable within the opening in the housing and along the longitudinal axis between a retracted position and an extended position with respect to the housing;
the collar comprises at least one retaining tab extending in a direction substantially normal to the longitudinal axis of the collar and configured to contact a bumper of the housing when in the extended position to prohibit the collar from sliding out of the housing; and
the collar is configured to receive and surround a portion of the removable device;
a collar flange on a second end of the collar comprising a substantially planar first mating surface, wherein:
the collar flange and the first mating surface are substantially normal to the longitudinal axis of the bore of the collar; and
the collar flange forms at least one slot configured to accept a corresponding tab of the removable device; and
a cover comprising a substantially planar second mating surface and a pair of sidewalls, each of the sidewalls comprising a portion that is substantially parallel to the second mating surface, wherein:
the cover comprises a main opening comprising a locked opening portion of a smaller diameter than an unlocked opening portion;
the unlocked opening portion is at least partially defined by an unlock edge configured to allow the tab of the removable device to pass through the unlocked opening portion and into the at least one slot of the collar flange;
the locked opening portion is at least partially defined by a lock edge;
the second mating surface is slideable in a plane over the first mating surface to lock the removable device within the collar and the locked opening portion when the lock edge of the cover slides over the tab of the removable device;
the sidewalls form channels configured to attach the cover to the collar flange; and
the collar and the cover are configured to slide together along the longitudinal axis with respect to the housing.

2. The system of claim 1, wherein the first mating surface comprises a guide structure for engaging the sidewalls of the cover.

3. The system of claim 1, wherein the collar flange comprises at least one first locking structure and the cover comprises at least one second locking structure capable of engaging the at least one first locking structure on the collar flange to releasably attach the device to the collar.

4. The system of claim 3, wherein:
the first mating surface comprises at least one detent, and
the second mating surface comprises at least one indent configured to mate with the at least one detent.

5. The system of claim 4, wherein a height of the detent is between approximately 0.0127 centimeters and 0.127 centimeters and a depth of the indent is between approximately 0.0254 centimeters and 0.0889 centimeters.

6. The system of claim 1, wherein the cover is configured to slide horizontally within the plane with respect to the collar flange to lock and unlock the removable device.

7. The system of claim 1, wherein the cover is configured to rotate within the plane with respect to the collar flange to lock and unlock the removable device.

8. The system of claim 1, further comprising an o-ring attached to the collar and configured to contact at least a portion of the opening in the housing.

9. The system of claim 1, wherein the removable device is a cystoscope comprising a probe configured to be inserted in the opening running through the housing.

10. A system for releasably attaching a removable device, the system comprising:
an elongate collar comprising a longitudinal bore having a longitudinal axis, wherein:
a first end of the collar is configured to engage an opening in a housing of a medical device;
the collar is configured to be slideable within the opening in the housing and along the longitudinal axis between a retracted position and an extended position with respect to the housing;
the collar comprises at least one retaining tab extending in a direction substantially normal to the longitudinal axis of the collar and configured to contact a bumper of the housing when in the extended position to prohibit the collar from sliding out of the housing; and
the collar is configured to receive and surround a portion of the removable device;
a collar flange on a second end of the collar comprising a substantially planar first mating surface, wherein:
the collar flange and the first mating surface are substantially normal to the longitudinal axis of the bore of the collar; and
the collar flange forms at least one slot configured to accept a corresponding tab of the removable device; and
a cover comprising a substantially planar second mating surface and a pair of sidewalls, each of the sidewalls comprising a portion that is substantially parallel to the second mating surface, wherein:
the cover comprises a main opening comprising a locked opening portion of a smaller diameter than an unlocked opening portion;
the unlocked opening portion is at least partially defined by an unlock edge configured to allow the tab of the removable device to pass through the unlocked opening portion and into the at least one slot of the collar flange;
the locked opening portion is at least partially defined by a lock edge;
the second mating surface is slideable in a plane over the first mating surface to lock the removable device within the collar and the locked opening portion when the lock edge of the cover slides over the tab of the removable device;
the sidewalls form channels configured to attach the cover to the collar flange; and
the collar and the cover are configured to slide together along the longitudinal axis with respect to the housing;
wherein the first mating surface comprises a guide structure for engaging the sidewalls of the cover; and
wherein the guide structure comprises a pair of opposed substantially parallel guide tabs.

11. The system of claim 10, wherein the guide structure comprises a guide tab.

12. The system of claim 10, wherein the portion of each of the pair of sidewalls comprise a retaining flange extending substantially normal to the sidewalls and substantially parallel to the second mating surface.

13. The system of claim 10, wherein the collar further comprises at least one retaining structure comprising the at least one retaining tab and configured to engage the opening of the housing to limit movement of the collar along the longitudinal axis of the collar within the opening in the housing.

14. The system of claim 10, wherein the collar flange comprises at least one first locking structure and the cover comprises at least one second locking structure capable of engaging the at least one first locking structure on the collar flange to releasably attach the device to the collar.

15. The system of claim 14, wherein the first mating surface comprises at least one male locking structure.

16. The system of claim 15, wherein the second mating surface comprises at least one female locking structure configured to mate with the at least one male locking structure.

17. A system for releasably attaching a device, the system comprising:
an elongate collar comprising a longitudinal bore having a longitudinal axis, wherein:
a first end of the collar is configured to engage an opening in a housing of a medical device;
the collar is configured to be slideable within the opening in the housing and along the longitudinal axis between a retracted position and an extended position with respect to the housing;
the collar comprises at least one retaining tab extending in a direction substantially normal to the longitudinal axis of the collar and configured to contact a bumper of the housing when in the extended position to prohibit the collar from sliding out of the housing; and
the collar is configured to receive and surround a portion of the removable device;
a collar flange on a second end of the collar comprising a substantially planar first mating surface, wherein:
the collar flange and the first mating surface are substantially normal to the longitudinal axis of the bore of the collar; and
the collar flange forms at least one slot configured to accept a corresponding tab of the removable device; and
a cover comprising a substantially planar second mating surface and a pair of sidewalls, each of the sidewalls comprising a portion that is substantially parallel to the second mating surface, wherein:
the cover comprises a main opening comprising a locked opening portion of a smaller diameter than an unlocked opening portion;
the unlocked opening portion is at least partially defined by an unlock edge configured to allow the tab of the removable device to pass through the unlocked opening portion and into the at least one slot of the collar flange;
the locked opening portion is at least partially defined by a lock edge;
the second mating surface is slideable in a plane over the first mating surface to lock the removable device within the collar and the locked opening portion when the lock edge of the cover slides over the tab of the removable device;
the sidewalls form channels configured to attach the cover to the collar flange; and
the collar and the cover are configured to slide together along the longitudinal axis with respect to the housing;
wherein:
the cover further comprises at least one limit flange that limits movement of the cover with respect to the collar flange,
the limit flange is substantially normal to the second mating surface,
the limit flange engages an edge region of the collar flange, and
the edge region is substantially normal to a plane of the first mating surface of the collar flange.

18. The system of claim 17, wherein the cover comprises a pair of opposed limit flanges.

19. A system for releasably attaching a removable device, the system comprising:
an elongate collar comprising a longitudinal bore having a longitudinal axis, wherein:
a first end of the collar is configured to engage an opening in a housing of a medical device;
the collar is configured to be slideable within the opening in the housing and along the longitudinal axis between a retracted position and an extended position with respect to the housing;
the collar comprises a pair of opposed parallel retaining tabs extending in opposite directions substantially normal to the longitudinal axis of the collar and configured to contact respective bumpers of the housing when in the extended position to prohibit the collar from sliding out of the housing; and
the collar is configured to receive and surround a portion of the removable device;
a collar flange on a second end of the collar comprising a substantially planar first mating surface, wherein:
the collar flange and the first mating surface are substantially normal to the longitudinal axis of the bore of the collar; and
the collar flange forms at least one slot configured to accept a corresponding tab of the removable device; and
a cover comprising a substantially planar second mating surface and a pair of sidewalls, each of the sidewalls comprising a portion that is substantially parallel to the second mating surface, wherein:
the cover comprises a main opening comprising a locked opening portion of a smaller diameter than an unlocked opening portion;
the unlocked opening portion is at least partially defined by an unlock edge configured to allow the tab of the removable device to pass through the unlocked opening portion and into the at least one slot of the collar flange;
the locked opening portion is at least partially defined by a lock edge;
the second mating surface is slideable in a plane over the first mating surface to lock the removable device within the collar and the locked opening portion when the lock edge of the cover slides over the tab of the removable device;
the sidewalls form channels configured to attach the cover to the collar flange; and
the collar and the cover are configured to slide together along the longitudinal axis with respect to the housing.

20. The system of claim 19, further comprising a retaining structure comprising the retaining tabs and respective substantially planar guide regions extending along an exterior surface of the collar and substantially parallel to the longitudinal axis of the collar, wherein the guide regions extend from each respective retaining tab to the collar flange.

21. A system for releasably attaching a removable device to a housing, the system comprising:
an elongate collar comprising a longitudinal bore for receiving the device through the bore, wherein:
a first end of the collar is configured to engage an opening in the housing of a medical device;
the collar is configured to be slideable within the opening in the housing and along the longitudinal axis between a retracted position and an extended position with respect to the housing;
the first end of the collar comprises at least one retaining structure that extends in a direction normal to a longitudinal axis of the bore of the collar, the at least one retaining structure being configured to engage an opening of the housing;
the retaining structure is configured to contact a bumper of the housing when in the extended position to prohibit the collar from sliding out of the housing; and
the collar is configured to receive and surround a portion of the removable device;
a collar flange on a second end of the collar comprising a substantially planar first mating surface, wherein:
the collar flange and the first mating surface are substantially normal to the longitudinal axis of the bore of the collar; and
the collar flange forms at least one slot configured to accept a corresponding tab of the removable device; and
a cover comprising a substantially planar second mating surface and a pair of sidewalls each comprising a portion that is substantially parallel to the second mating surface in which the sidewalls form channels configured to attach to the collar flange, wherein:
the cover comprises a main opening comprising a locked opening portion of a smaller diameter than an unlocked opening portion;
the unlocked opening portion is at least partially defined by an unlock edge configured to allow the tab of the removable device to pass through the unlocked opening portion and into the at least one slot of the collar flange;
the locked opening portion is at least partially defined by a lock edge;
the second mating surface is slideable in a plane over the first mating surface to lock the removable device within the collar and the locked opening portion when the lock edge of the cover slides over the tab of the removable device;
the sidewalls form channels configured to attach the cover to the collar flange; and
the collar and the cover are configured to slide together along the longitudinal axis with respect to the housing.

22. The system of claim 21, wherein the first mating surface comprises a guide structure for engaging the sidewalls of the cover.

23. The system of claim 22, wherein the guide structure comprises a guide tab.

24. The system of claim 22, wherein the guide structure comprises a pair of opposed substantially parallel guide tabs.

25. The system of claim 22, wherein the guide structure is substantially circular around the collar flange.

26. The system of claim 22, wherein the portion of each of the sidewalls comprises a retaining flange extending substantially normal to the sidewalls and substantially parallel to the second mating surface.

27. The system of claim 21, wherein the cover further comprises at least one limit flange that limits movement of the cover with respect to the collar flange, wherein the limit flange is substantially normal to the second mating surface, and wherein the limit flange engages an edge region of the collar flange, and wherein the edge region is substantially normal to a plane of the first mating surface of the collar flange.

28. The system of claim 21, wherein the collar flange comprises at least one first locking structure and the cover comprises at least one second locking structure capable of engaging the at least one first locking structure on the collar flange to releasably attach the device.

29. The system of claim 21, wherein the first mating surface comprises at least one male locking structure.

30. The system of claim 29, wherein the second mating surface comprises at least one female locking structure configured to mate with the at least one male locking structure.

31. A system for releasably attaching a removable device to a housing, the system comprising:
an elongate collar comprising a longitudinal bore for receiving the removable device through the bore, wherein:
a first end of the collar comprises at least one retaining structure that extends in a direction normal to a longitudinal axis of the bore of the collar, the at least one retaining structure being configured to engage an opening of the housing;
the collar is configured to be slideable within the opening in the housing and along the longitudinal axis between a retracted position and an extended position with respect to the housing;
the at least one retaining tab is configured to contact a bumper of the housing when in the extended position to prohibit the collar from sliding out of the housing; and
the collar is configured to receive and surround a portion of the removable device;
a collar flange disposed on a second end of the collar comprising a substantially planar first mating surface, wherein:
the collar flange and first mating surface are substantially normal to the longitudinal axis of the bore of the collar,
a first portion of the collar flange is attached to the second end of the collar, and
the collar flange forms at least one slot configured to accept a corresponding tab of the removable device; and
a cover comprising a substantially planar second mating surface coupled to the first portion of the collar flange, wherein:
the cover comprises a main opening comprising a locked opening portion of a smaller diameter than an unlocked opening portion;
the unlocked opening portion is at least partially defined by an unlock edge configured to allow the tab of the removable device to pass through the unlocked opening portion and into the at least one slot of the collar flange;
the locked opening portion is at least partially defined by a lock edge;

the second mating surface is slideable in a plane over the first mating surface to lock the removable device within the collar and the locked opening portion when the lock edge of the cover slides over the tab of the removable device;

the sidewalls form channels configured to attach the cover to the collar flange; and the collar and the cover are configured to slide together along the longitudinal axis with respect to the housing.

32. The system of claim 31, wherein a second portion of the collar flange comprises a ramped tab that extends in a direction normal to the longitudinal axis of the bore of the collar.

33. The system of claim 32, wherein the second portion of the collar flange flexes in a direction normal to the longitudinal axis of the bore of the collar when force is applied to the ramped tab.

* * * * *